US009486520B2

(12) United States Patent
Borrebaeck et al.

(10) Patent No.: US 9,486,520 B2
(45) Date of Patent: Nov. 8, 2016

(54) COMPOSITIONS COMPRISING POLYGLUTAMIC ACID NANOPARTICLES AND CD40 AGONISTS

(75) Inventors: Carl Arne Krister Borrebaeck, Lund (SE); Sissela Rachel Linn Broos, Malmo (SE); Peter Bo Joakim Ellmark, Lund (SE); Malin Marie Lindstedt, Bunkeflostrand (SE)

(73) Assignee: Alligator Bioscience AB, Lund (SE)

( * ) Notice: Subject to any disclaimer, the term of this patent is extended or adjusted under 35 U.S.C. 154(b) by 120 days.

(21) Appl. No.: 13/639,406

(22) PCT Filed: Apr. 13, 2011

(86) PCT No.: PCT/GB2011/000577
§ 371 (c)(1),
(2), (4) Date: Oct. 4, 2012

(87) PCT Pub. No.: WO2011/128642
PCT Pub. Date: Oct. 20, 2011

(65) Prior Publication Data
US 2013/0028932 A1    Jan. 31, 2013

(30) Foreign Application Priority Data
Apr. 13, 2010 (GB) .................................. 1006096.0

(51) Int. Cl.
*A61K 39/395* (2006.01)
*A61K 39/39* (2006.01)
*A61K 9/00* (2006.01)
*A61K 9/14* (2006.01)
*A61K 9/51* (2006.01)
*A61K 39/00* (2006.01)

(52) U.S. Cl.
CPC ............. *A61K 39/39* (2013.01); *A61K 9/0019* (2013.01); *A61K 9/146* (2013.01); *A61K 9/5146* (2013.01); *A61K 2039/55516* (2013.01); *A61K 2039/55555* (2013.01)

(58) Field of Classification Search
None
See application file for complete search history.

(56) References Cited

U.S. PATENT DOCUMENTS

| 4,816,567 A | 3/1989 | Cabilly et al. | |
|---|---|---|---|
| 7,785,612 B2 * | 8/2010 | Akashi et al. | 424/280.1 |
| 2007/0237831 A1 * | 10/2007 | Sung et al. | 424/490 |
| 2010/0239575 A1 * | 9/2010 | Banchereau et al. | 424/133.1 |

FOREIGN PATENT DOCUMENTS

| EP | 1 857 489 A1 | 11/2007 |
|---|---|---|
| EP | 1 932 538 A1 | 6/2008 |
| WO | WO-2010/024676 A1 | 3/2010 |

OTHER PUBLICATIONS

Akagi et al., J. Biomater. Sci. Polymer Edn. 17:875-892, 2006.*
Ahonen, C.L. et al. (Mar. 15, 2008, e-pub. Jan. 17, 2008). "Enhanced Efficacy and Reduced Toxicity of Multifactorial Adjuvants Compared with Unitary Adjuvants as Cancer Vaccines," *Blood* 111(6):3116-3125.
Akagi, T. et al. (2005, e-pub. Aug. 24, 2005). "Preparation and Characterization of Biodegradable Nanoparticles Based on Poly(γ-glutamic acid) with 1-phenylalanine as a protein Carrier," *Journal of Controlled Release* 108(2-3):226-236.
Alexis, F. et al (2008). "Factors Affecting the Clearance and Biodistribution of Polymeric Nanoparticles," *Molecular Pharmaceutics* 5(4):505-515.
Avgoustakis, K. (2002). "PLGA-mPEG Nanoparticles of Cisplatin: In Vitro Nanoparticle Degradation, In Vitro Drug Release and In Vivo Drug Residence in Blood Properties," *Journal of Controlled Release* 79:123-135.
Avgoustakis, K. (2004). "Pegylated Poly(Lactide) and Poly(Lactide-Co-Glycolide) Nanoparticles: Preparation, Properties and Possible Applications in Drug Delivery," *Current Drug Delivery* 1:321-333.
Bajoarth, J. (Sep. 18, 1998). "Detailed Comparison of Two Molecular Models of the Human CD40 Ligand with an X-ray Structure and Critical Assessment of Model-based Mutagenesis and Residue Mapping Studies," *The Journal of Biological Chemistry* 273(38):24603-24609.
Bajorath, J. et al. (1995). "Identification of Residues on CD40 and Its Ligand Which Are Critical for the Receptor—Ligand Interaction," *Biochemistry* 34(6):1833-1844.
Bajorath, J. et al. (1995). "Analysis of gp39/CD40 Interactions Using Molecular Models and Site-Directed Mutagenesis," *Biochemistry* 34(31):9884-9892.
Bishop, G.A. et al. (Jul. 2002). "Mechanisms of TNF Receptor-associated Factor (TRAF) Regulation in B Lymphocytes," *Journal of Leukocyte Biology* 72(1):19-23.
Boerner, P. et al. (Jul. 1, 1991). "Production of Antigen-Specific Human Monoclonal Antibodies from In Vitro-Primed Human Splenocytes," *The Journal of Immunology* 147:86-95.
Bugelski, P.J. et al. (2009). "Monoclonal Antibody-induced Cytokine-release Syndrome," *Expert Review of Clinical Immunology* 5(5):499-521.
Carlsson, R. et al. (2001). "n-CoDeR Concept: Unique Types of Antibodies for Diagnostic Use and Therapy," *Expert Review of Molecular Diagnostics* 1(1):102-108.
Cole, S.P.C. et al. (1984). "Human Monoclonal/Antibodies," *Molecular and Cellular Biochemistry* 62:109-120.
Costello, R.T. et al. (Nov. 1999). "What is the Real Role of CD40 in Cancer Immunotherapy?" *Immunology Today* 20(11):488-493.

(Continued)

*Primary Examiner* — Phillip Gambel
(74) *Attorney, Agent, or Firm* — Morrison & Foerster LLP

(57) ABSTRACT

The present invention provides pharmaceutical compositions comprising an immunostimulatory polypeptide and polyglutamic acid (PGA) nanoparticles, formulated in a pharmaceutically acceptable diluent, carrier or excipient. Such compositions have utility in stimulating the immune system in subjects, with the components capable of interacting synergistically. The invention further provides uses of the compositions of the invention, for example in the treatment of cancer, and kit and components for use in the same.

10 Claims, 8 Drawing Sheets

(56) References Cited

OTHER PUBLICATIONS

Figure 1:
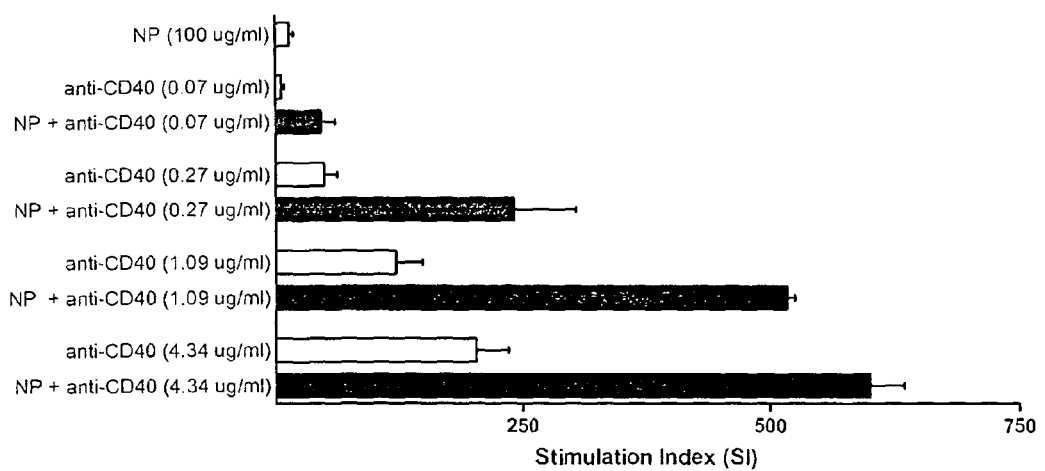

Cote, R.J. et al. (Apr. 1983). "Generation of Human Monoclonal Antibodies Reactive with Cellular Antigens," *Proceedings of the National Academy of Sciences of the United States of America* 80:2026-2030.

Debbage, P. (2009). "Targeted Drugs and Nanomedicine: Parent and Future," *Current Pharmaceutical Design* 15(2):153-172.

Diehl, L. et al. (Jul. 1999). "CD40 Activation In Vivo Overcomes Peptide-induced Peripheral Cytotoxic T-lymphocyte Tolerance and Augments Anti-tumor Vaccine Efficacy," *Nature Medicine* 5(7):774-779.

Dobrovolskaia, M.A. et al. (2008, e-pub. Jul. 1, 2009). "Preclinical Studies to Understand Nanoparticle Interaction with the Immune System and Its Potential Effects on Nanoparticle Biodistribution," *Molecular Pharmacology* 5:487-495.

Dominguez, A. et al. (Feb. 3, 2010, e-pub. Feb. 3, 2011). "Targeting the Tumor Microenvironment with Anti-neu/anti-CD40 Conjugated Nanoparticles for the Induction of Antitumor Immune Responses," *Vaccine* 28(5):1383-1390.

Ellmark, P. et al. (2008). "Identification of a Strongly Activating Human Anti-CD40 Antibody That Suppresses HIV Type 1 Infection," *AIDS Research and Human Retroviruses* 24(3):367373.

Ellmark, P. et al. (2002). "Modulation of the CD40-CD40 Ligand Interaction Using Human Anti-CD40 Single-chain Antibody Fragments Obtained from the n-CoDeR Phage Display Library," *Immunology* 106:456-463.

Francisco, J.A. et al. (Jun. 15, 2000). "Agonistic Properties and in Vivo Antitumor Activity of the Anti-CD40 Antibody SGN-14," *Cancer Research* 60(12):3225-3231.

Fransen, M.F. et al. (Apr. 15, 2011). "Local Activation of CD8 T Cells and Systemic Tumor Eradication without Toxicity via Slow Release and Local Delivery of Agonistic CD40 Antibody," *Clinical Cancer Research* 17(8):2270-2280.

French, R.R. et al. (May 1999). "CD40 Antibody Evokes a Cytotoxic T-cell Response that Eradicates Lymphoma and Bypasses T-cell Help," *Nature Medicine* 5(5):548-553.

Geldart, T. et al. (Aug. 2005). "Anti-CD40 Monoclonal Antibody," *Leukemia & Lymphoma* 46(8):1105-1113.

Gladue, R.P. (2008). "Presentation: In Vivo Efficacy of the CD40 Agonist Antibody, CP-870,893 Against a Broad Range of Tumor Types: Impact of Tumor CD40 Expression, Dendritic Cells, and Chemotherapy," *ASCO*, twenty-two pages.

Hamasaki, T. et al. (May 2010). "Modulation of Gene Expression Related to Toll-Like Receptor Signaling in Dendritic Cells by Poly(y-Glutamic Acid) Nanoparticles," *Clinical and Vaccine Immunology* 17(5):748-756.

Haswell, L.E. et al. (2001). "Analysis of the Oligomeric Requirement for Signaling by CD40 Using Soluble Multimeric Forms of its Ligand, CD154," *European Journal of Immunology* 31(10):3094-3100.

Hatzifoti, C. et al. (Jun. 2008). "Liposomal Co-Entrapment of CD40mAb Induces Enhanced IgG Responses against Bacterial Polysaccharide and Protein," *PLoS One* 3(6):e2368, 1-8.

Hoogenboom, H.R. et al. (1992). "By-passing Immunisation Human Antibodies from Synthetic Repertoires of Germline V-H Gene Segments Rearranged In Vitro," *The Journal of Molecular Biology* 227:381-388.

Hunter, T.B. et al. (2007). "An Agonist Antibody Specific for CD40 Induces Dendritic Cell Maturation and Promotes Autologous Antitumour T-cell Responses in an in vitro Mixed Autologous Tumour Cell/Lymph Node Cell Model," *Scandinavian Journal of Immunology* 65(5):479-486.

Jackaman, C. et al. (2008, e-pub. Sep. 29, 2008). "Deliberately Provoking Local Inflammation Drives Tumors to Become Their Own Protective Vaccine Site," *International Immunology* 20(11):1467-1479.

Jones, P.T. et al. (May 29, 1986). "Replacing the Complementarity-determining Regions in a Human Antibody with Those From a Mouse," *Nature* 321:522-525.

Kelley, S.K. et al. (2006). "Preclinical Pharmacokinetics, Pharmacodynamics, and Activity of a Humanized anti-CD40 Antibody (SGN-40) in Rodents and Non-human Primates," *British Journal of Pharmacology* 148(8):1116-1123.

Khalil, M. et al. (Jun. 1, 2007, e-pub. Jul. 7, 2009). "Anti-CD40 Agonist Antibodies: Preclinical and Clinical Experience," *Update on Cancer Therapeutics* 2(2):61-65.

Kohler, G. et al. (Aug. 7, 1975). "Continuous Cultures of Fused Cells Secreting Antibody of Predefined Specificity," *Nature* 256:495-497.

Kozbor, D. et al. (1985). "Specific Immunoglobulin Production and Enhanced Tumorigenicity Following Ascites Growth of Human Hybridomas," *Journal of Immunology Methods* 81:31-42.

Law, C. et al. (Sep. 15, 2005, e-pub. Sep. 15, 2005). Preclinical Antilymphoma Activity of a Humanized Anti-CD40 Monoclonal Antibody, SGN-40, *Cancer Research* 65(18):8331-8338.

Ledbetter, J.A. et al. (1997). "Agonistic Activity of a CD40-Specific Single-Chain FV Constructed from the Variable Regions of mAb G28-5," *Critical Reviews in Immunology* 17(56):427-435.

Luqman, M. et al. (Aug. 1, 2008, e-pub. May 22, 2008). "The Antileukemia Activity of a Human Anti-CD40 Antagonist Antibody, HCD122, on Human Chronic Lymphocytic Leukemia Cells," *Blood* 112(3):711-720.

Marks, J.D. et al. (1991). "By-passing Immunization Human Antibodies from V-gene Libraries Displayed on Phage," *The Journal of Molecular Biology* 222:581-597.

Milano, F. et al. (2007, e-pub. Feb. 5, 2007). "An Improved Protocol for Generation of Immuno-potent Dendritic Cells Through Direct Electroporation of CD14+ Monocytes," *Journal of Immunological Methods* 321(1-2):94-106.

Naismith, J.H. et al. (Feb. 1998). "Modularity in the TNF-receptor Family," *Trends in Biochemical Sciences* 23:74-79.

Oflazoglu, E. et al. (2009, e-pub. Dec. 9, 2008). "Macrophages and Fc-receptor Interactions Contribute to the Antitumour Activities of the Anti-CD40 Antibody SGN-40," *British Journal of Cancer* 100(1):1 13-117.

Okamoto, S. et al. (2007, e-pub Oct. 11, 2007). "Influenza Hemagglutinin Vaccine with Poly(y-glutamic acid) Nanoparticles Enhances the Protection against Influenza Virus Infection Through Both Humoral and Cell-mediated Immunity," *Vaccine* 25(49):8270-8278.

Orlandi, R. et al. (May 1989). "Cloning Immunoglobulin Variable Domains for Expression by the Polymerase Chain Reaction," *Proceedings of the National Academy of Sciences of the United States of America* 86:3833-3837.

Pound, J.D. et al. (1999). "Minimal Cross-linking and Epitope Requirements for CD40-dependent Suppression of Apoptosis Contrast with Those for Promotion of the Cell Cycle and Homotypic Adhesions in Human B Cells," *International Immunology* 1999 11(1):11-20.

Presta, L.G. (1992). "Antibody Engineering," *Current Opinion in Structural Biology* 2:593-596.

Pullen, S.S. et al. (May 14, 1999). "CD40 Signaling through Tumor Necrosis Factor Receptor-associated Factors (TRAFs)," *The Journal of Biological Chemistry* 274(20):1424614254.

Pullen, S.S. et al. (1999, e-pub. Jul. 15, 1999). "High-Affinity Interactions of Tumor Necrosis Factor Receptor-Associated Factors (TRAFs) and CD40 Require TRAF Trimerization and CD40 Multimerization," *Biochemistry* 38(31):10168-10177.

Quezada, S.A. et al. (2004, e-pub Oct. 15, 2003). "CD40/CD154 Interactions at the Interface of Tolerance and Immunity," *Annual Review of Immunology* 22:307-328.

Riechmann, L. et al. (Mar. 24, 1988). "Reshaping Human Antibodies for Therapy," *Nature* 332:323-329.

Schonbeck, U. et al. (2001). "The CD40/CD154 Receptor/ligand Dyad," *Cellular and Molecular Life Sciences* 58(1):4-43.

Singh, J. et al. (1998). "The Role of Polar Interactions in the Molecular Recognition of CD40L with its Receptor CD40," *Protein Science* 7(5):1124-1135.

(56) References Cited

OTHER PUBLICATIONS

Sotomayor, E.M. et al. (Jul. 1999). "Conversion of Tumor-specific CD4+ T-cell Tolerance to T-cell Priming Through in vivo Ligation of CD40," *Nature Medicine* 5(7):780-787.

Staveley-O'Carroll, K. et al. (2003). "In Vivo Ligation of CD40 Enhances Priming Against the Endogenous Tumor Antigen and Promotes CD8 T Cell Effector Function in SV40 T Antigen Transgenic Mice," *The Journal of Immunology* 171(2):697-707.

Tai, Y.T. et al. (Apr. 1, 2003, e-pub Nov. 14, 2002). "CD40 Induces Human Multiple Myeloma Cell Migration Via Phosphatidylinositol 3—kinase/AKT/NF-kB Signaling," *Blood* 101(7):2762-2769.

Tai, Y.T. et al. (2004, e-pub Apr. 15, 2004). "Mechanisms by which SGN-40, a Humanized Anti-CD40 Antibody, Induces Cytotoxicity in Human Multiple Myeloma Cells: Clinical Implications," *Cancer Research* 64(8):2846-2852.

Tai, Y.T. et al. (2005, e-pub Jul. 1, 2005). "Human Anti-CD40 Antagonist Antibody Triggers Significant Antitumor Activity against Human Multiple Myeloma," *Cancer Research* 65(13):5898-5906.

Uto, T. et al. (2007). "Targeting of Antigen to Dendritic Cells with Poly(y-Glutamic Acid) Nanoparticles Induces Antigen-Specific Humoral and Cellular Immunity," *The Journal of Immunology* 178(5):2979-2986.

Van Kooten, C. et al. (Jan. 2000). "CD40-CD40 Ligand," *Journal of Leukocyte Biology* 67(1):2-17.

Van Mierlo, G.J.D. et al. (Apr. 16, 2002). "CD40 Stimulation Leads to Effective Therapy of CD40—tumors Through Induction of Strong Systemic Cytotoxic T Lymphocyte Immunity," *Proceedings of the National Academy of Sciences of the United States of America* 99(8):55615566.

Van Mierlo, G.J.D. et al. (2004). "Activation of Dendritic Cells That Cross-Present Tumor-Derived Antigen Licenses CD8' Ctl to Cause Tumor Eradication," *The Journal of Immunology* 173(1 1):6753-6759.

Verhoeyen, M. et al. (Mar. 25, 1988). "Reshaping Human Antibodies: Grafting an Antilysozyme Activity," *Science* 239:1534-1536.

Vonderheide, R.H. et al. (Jul. 1, 2001). "Phase I Study of Recombinant Human CD40 Ligand in Cancer Patients," *Journal of Clinical Oncology* 19(13):3280-3287.

Vonderheide, R.H. et al. (Feb. 15, 2007, e-pub Feb. 22, 2007). "Prospect of Targeting the CD40 Pathway for Cancer Therapy," *Clinical Cancer Research* 13(4):1083-1088.

Vonderheide, R.H. et al. (Mar. 1, 2007). "Clinical Activity and Immune Modulation in Cancer Patients Treated With CP-870,893, a Novel CD40 Agonist Monoclonal Antibody," *Journal of Clinical Oncology* 25(7):876-883.

Wang, X. et al. (2008). "Poly(y-Glutamic Acid) Nanoparticles as an Efficient Antigen Delivery and Adjuvant System: Potential for an AIDS Vaccine," *Journal of Medical Virology* 80(1):11-9.

Werneburg, B.G. et al. (Nov. 16, 2001). "Molecular Characterization of CD40 Signaling Intermediates," *The Journal of Biological Chemistry* 276(46):43334-43342.

Winter, G. et al. (Jan. 24, 1991). "Man-made Antibodies," *Nature* 349:293-299.

Yamaguchi, S. et al. (2010, e-pub. Nov. 27, 2009). "EphA2-derived Peptide Vaccine with Amphiphilic Poly(y-glutamic acid) Nanoparticles Elicits an Anti-tumor Effect Against Mouse Liver Tumor," *Cancer Immunol Immunother* 59(5):759-767.

International Search Report mailed on Jul. 26, 201, for PCT Application No. PCT/GB2011/000577 filed on Apr. 13, 2011, 4 pages.

Written Opinion of the International Searching Authority mailed on Jul. 26, 2011, for PCT Application No. PCT/GB2011/000577 filed on Apr. 13, 2011, 5 pages.

International Preliminary Report on Patentability mailed on Oct. 16, 2012, for PCT Application No. PCT/GB2011/000577 filed on Apr. 13, 2011, 6 pages.

\* cited by examiner (A)

(B)

(C)

COMPOSITIONS COMPRISING POLYGLUTAMIC ACID NANOPARTICLES AND CD40 AGONISTS

CROSS-REFERENCE TO RELATED APPLICATIONS

This application is a National Phase application under 35 U.S.C. §371 of International Application No. PCT/GB2011/000577 filed Apr. 13, 2011 and claims the benefit of Great Britain Application No. 1006096.0 filed Apr. 13, 2010, the disclosures of which are incorporated herein by reference in their entirety.

FIELD OF INVENTION

The present invention relates to compositions for use in stimulating the immune system of a subject, for example in the treatment of cancer or viral infection or during vaccination.

BACKGROUND

Cancer Immunotherapy

Cancer is the second leading cause of death in developed countries. The treatment of certain tumors has improved significantly the last decades. However, conventional cancer therapies such as surgery, radiotherapy and chemotherapy need to be complemented by alternative approaches, particularly for disseminated cancer forms. One promising approach is cancer immunotherapy, which aims at inducing an effective and specific immune response that can control and destroy the cancer cells.

Even if cancer cells often evoke a specific immune response, the response is normally not sufficient to eliminate the malignant cells. This is due to tumor-mediated immunosuppressive mechanisms that block the anti-tumor immune response[1]. However, these suppressive mechanisms can be reversed by immunotherapeutic strategies aiming at 1) activating professional antigen presenting cells (APC) such as dendritic cells (DC) via e.g. CD40 or Toll-like receptors (TLR), 2) using cytokines, such as IL-2, IL-12 and IFN-α to stimulate the lymphocytes, or 3) blocking signals that suppresses T cell activation by targeting e.g. Cytotoxic T-Lymphocyte Antigen 4 (CTLA-4) or inhibitory receptor programmed death 1 (PD-1).

Immunotherapy is already in use for treatment of e.g. bladder carcinoma and malignant melanoma. It has been demonstrated that the cytokine milieu in bladder cancer has an immunosuppressive profile, which makes it a good target for immunotherapeutic intervention[2]. In fact, intravesical treatment with live, attenuated *bacillus* Calmette Guerin (BCG) is routinely used for immunotherapy in bladder cancer[2]. A number of immunotherapies have been tried also for treatment of malignant melanoma. Immunotherapeutic approaches using tumor-infiltrating T lymphocyte infusion in combination with a high-dose of IL-2 have been shown to produce a significant objective response. However, there is a great need for more effective immunotherapeutic strategies for these indications.

The CD40 plays a central role in the immune system, which makes it a highly interesting target for immunotherapy. It is a member of the tumor necrosis factor receptor (TNFR) family and is expressed on a variety of cells in the immune system, such as B cells, monocytes and dendritic cells, whereas the CD40 ligand (CD40L) is mainly expressed on activated T-cells[3]. CD40L-mediated signalling triggers several biological events, including activation, proliferation, rescue from apoptosis, and production of cytokines and chemokines[3]. In immunotherapeutic settings, including animal models and clinical trials, anti-CD40 antibodies have been used for direct stimulation of the CD40[3-6], to block the CD40-CD40L interaction for treatment of autoimmune disorders, or by direct targeting of tumor cells[7, 8]. Anti-CD40 antibodies have been described as being agonistic, i.e. able to activate cells via the CD40, or being antagonistic, i.e. able to block CD40L induced activation of the CD40. For immunotherapeutic applications aiming at activating the immune response or break tolerance, a strongly agonistic antibody is sought for. Methods that can improve the stimulatory/activating efficacy of such antibody would be highly advantageous.

The CD40 is a type I membrane protein that plays a central role in the immune system. It is a member of the tumor necrosis factor receptor (TNFR) family and is expressed on a variety of cells, e.g. B cells and dendritic cells (DC) as well as several types of carcinoma[1,2]. The CD40 ligand (CD40L) is mainly expressed on activated Tcells[1-7]. CD40L-mediated signalling triggers several biologic events, including immune, cell activation, proliferation, and production of cytokines and chemokines (reviewed by[1,2]). In addition, it can also induce apoptosis in several cancer cells (reviewed by[8-10]).

It has been shown that the minimal requirement to induce a signal through CD40 is the formation of a receptor dimer[11] and that the strength of the receptor mediated signal correlates with increasing valency of an extracellularly applied ligand[12]. Intracellular signal transmission through CD40 depends on adapter molecules (most notably the TNFR associated factor (TRAF) family) that interact with different intracellular recognition motifs[13-15]. Extracellular cross-linking of CD40 leads to a stabilisation of these intracellular adaptor molecules, which in turn initiate the signalling cascade.

The effect of CD40 agonists is twofold: i) Immune activation resulting in a tumor specific T cell response, and ii) direct apoptotic effect on CD40 expressing tumors (depending on tumor type). In many studies it has been difficult to separate the mechanisms, but it has been demonstrated that CD40 agonists have anti-tumor effects also on CD40 negative tumors[16]. CD40 stimulation also has the potential to be used as adjuvant in cancer vaccines.

Pre-clinical studies have demonstrated proof of concept for agonistic anti-CD40 antibody treatment of several cancer types[16-21]. It has been demonstrated to have an anti-tumor effect on lymphomas, melanoma, hepatoma, osteosarcoma, renal cell carcinoma breast cancer etc. In addition to the potent anti-tumor effect, it has been shown that systemic anti-CD40 treatment also results in side effects (shock syndrome, cytokine release syndrome (CRS)). However, these side effects were not seen when the anti-CD40 antibody was injected directly into the tumor, yet it resulted in systemic anti-tumor effect[16]. Mice treated intratumorally in one flank were able to clear tumors in the opposite flank[16]. This anti-tumor effect depends on DC activation and subsequent activation of a CTL response[21], which also resulted in a protective immunity to tumor re-challenge. These results have been verified by Jackaman et al[22]. They studied intratumoral injection of anti-CD40 antibodies alone or in combination with IL-2 in a malignant mesothelioma model (C57BL/6J).

Several humanized or human anti-CD40 antibodies have been evaluated in pre-clinical models[23-31]. These antibodies have mainly been evaluated in vivo in models based on human tumors xenografted into SCID mice. The effect on CD40 negative tumors has been demonstrated in one study, using SCID repopulated with human monocyte-derived dendritic cells (monocyte-derived dendritic cells) and naïve T cells (Gladue, 2008, ASCO).

Thus, the overwhelming majority of pre-clinical studies using CD40 agonist in cancer therapy have demonstrated a very potent anti-tumor effect. Local, intratumoral CD40 stimulation has been demonstrated to generate a systemic antitumor and metastasis clearing effect, without the side effects associated with systemic CD40 stimulation.

Anti-CD40 treatment has generated promising result in phase I clinical trials, and objective clinical responses have been reported for every anti-CD40 protein drug tested so far[10]. The CD40 agonists that have been in clinical trials for cancer therapy (recently reviewed by Vonderheide[10;32]) include CD40L (Avrend™)[33], one strong agonistic anti-CD40 antibody (CP-870,893 from Pfizer)[34] and one weak agonist (SGN-40, dacetuzumab, Seattle Genetics/Genentech).

Nanoparticles

Nanoparticles, i.e. particles with a diameter typically of approximately 100 to 300 nm, are novel tools with great potential in the field immunotherapy. They can be used as efficient transporters of biomolecules, such as DNA, RNA or proteins either attached to the surface or encapsulated within the particles. Different nanoparticle variants have shown great potential, both for sustained release of carried biomolecules and for activation of antigen presenting cells for induction of a cytotoxic T lymphocyte (CTL) response[10]. Several different particle types are currently evaluated in nanomedical applications, such as polystyrene particles, poly (lactic-co-glycolic acid) (PLGA) particles and poly (γ-glutamic acid) (γ-PGA) particles. Polystyrene particles have been shown to be effective in generating DC maturation[11], however, they are not biodegradable and therefore less suitable for therapeutic applications. PLGA particles on the other hand are fully biodegradable, however, there are problems associated with this method, such as low encapsulation efficiency of water-soluble proteins and instability arising during the formulation, storage and lyophilization of the nanoparticles. Recently, a novel protein delivery system has been described based on self-assembled amphiphilic polymeric γ-PGA nanoparticles, which are fully biodegradable[36]. It has been demonstrated that these particles are efficient for protein delivery and can be used to induce a specific T cell response in a vaccine model system[10].

Slow release compositions comprising an anti-CD40 antibody encapsulated in dextran-based particles, for use in cancer treatment, have also been reported[45]. The dextran particles used were in the microscale-range and were constructed to encapsulate the antibodies within the particles. The objectives with such slow-release formulations in local administration approaches are several, including minimization of antibody leakage from the local area to be treated, in order to reduce toxicity and other adverse effects associated with the systemic release of the antibody. In addition, slow-release may achieve reduced dosing frequency.

Despite the above developments in the fields of immunotherapy and nanoparticle use, there remains a need for new therapies for stimulating the immune system, in particular in the treatment of cancer.

SUMMARY OF INVENTION

The first aspect of the invention provides a pharmaceutical composition comprising:
(a) an immunostimulatory polypeptide; and
(b) nanoparticles;
in a pharmaceutically acceptable diluent, carrier or excipient,
wherein the nanoparticles comprise or consist of polyglutamic acid (PGA).

As used herein, 'pharmaceutical composition' means a therapeutically effective formulation according to the invention.

A 'therapeutically effective amount', or 'effective amount', or 'therapeutically effective', as used herein, refers to that amount which provides a therapeutic effect (e.g. stimulation of the immune system) for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

It will be appreciated by persons skilled in the art that such an effective amount of the composition of the invention may be delivered as a single bolus dose (i.e. acute administration) or, more preferably, as a series of doses over time (i.e. chronic administration). The effective amount of the composition may also be delivered by local or systemic administration.

In one embodiment, the immunostimulatory polypeptide and the nanoparticles are provided as a mixture (i.e. the components are not covalently linked to each other or encapsulated within each other, e.g. immunostimulatory polypeptide encapsulated within the nanoparticles). Such mixtures may conveniently be produced by simple mixing of the two components, optionally with a wash step, thus allowing a fast and robust protocol that avoids the need for solvents that may damage the integrity of the component immunostimulatory polypeptide (see Examples below).

It will be appreciated by persons skilled in the art that the mixed components, although initially formulated in the composition separately, may nevertheless associate or adsorb onto each other non-covalently. Thus, in one embodiment some or all of the immunostimulatory polypeptide molecules may be non-covalently immobilised on the nanoparticles, for example adsorbed on to the surface of the nanoparticles. Such adsorption is very mild and causes less loss of functional activity of the immunostimulatory polypeptide (e.g. antibody) compared to protocols using chemical modifications such as covalent coupling or immobilization of antibody to the nanoparticle surface[36].

In one preferred embodiment, the composition is capable of exhibiting a synergistic immunostimulatory effect, in vitro and/or in vivo. By "synergistic", in this context, we mean that the composition comprising both components (a) and (b) activates the immune system (or a component thereof) to a greater extent than the additive immunostimulatory effect of components (a) and (b) administered on their own.

It will be appreciated by persons skilled in the art that the compositions of the invention are suitable for stimulating the immune system of a subject for a number of different purposes. Thus, the invention encompasses anticancer compositions, vaccine to compositions and antiviral compositions.

A first essential component of the compositions of the invention is an immunostimulatory polypeptide.

In one embodiment, the polypeptide is capable of activating professional antigen-presenting cells (APCs), such as dendritic cells (DCs). Identifying such polypeptides may be accomplished using methods well known in the art, for example as described in Baal J W et al. An improved protocol for generation of immuno-potent dendritic cells through direct electroporation of CD14+ monocytes. *J Immunol Methods* 2007; 321(1-2):94-106.

A composition according to claim 6 wherein the polypeptide is capable of activating CD40.

Alternatively, or additionally, the polypeptide may be capable of stimulating lymphocytes.

Again, polypeptides exhibiting such properties may be identified using methods well known in the art, for example as described in Pound J D et al. Minimal cross-linking and epitope requirements for CD40-dependent suppression of apoptosis contrast with those for promotion of the cell cycle and homotypic adhesions in human B cells. *Int Immunol* 1999; 11(1):11-20.

In one particular embodiment, the polypeptide component of the compositions of the invention is an antibody, or antigen-binding fragment of the same.

By "antibody" we include substantially intact antibody molecules, as well as chimaeric antibodies, humanised antibodies, human antibodies, single chain antibodies, bispecific antibodies (for example, with affinity for CD40 and another immunostimulatory receptor, such as CD137), antibody heavy chains, antibody light chains, homodimers and heterodimers of antibody heavy and/or light chains, and antigen binding fragments and derivatives of the same.

By "antigen-binding fragment" we mean a functional fragment of an antibody that is capable of binding to the same antigen as the intact 'parent' antibody.

For example, the antigen-binding fragment may be selected from the group consisting of Fv fragments (e.g. single chain Fv and disulphide-bonded Fv), Fab-like fragments (e.g. Fab fragments, Fab' fragments and F(ab)$_2$ fragments), single variable domains (e.g. $V_H$ and $V_L$ domains) and domain antibodies (dAbs, including single and dual formats [i.e. dAb-linker-dAb]).

Possible advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli*, thus allowing the facile production of large amounts of the said fragments.

Also included within the scope of the invention are modified versions of antibodies and antigen-binding fragments thereof, e.g. modified by the covalent attachment of polyethylene glycol or other suitable polymer.

Methods of generating antibodies and antibody fragments are well known in the art. For example, antibodies may be generated via any one of several methods which employ induction of in vivo production of antibody molecules, screening of immunoglobulin libraries (Orlandi. et al, 1989. *Proc. Natl. Acad. Sci. U.S.A.* 86:3833-3837; Winter et al., 1991, *Nature* 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:495-497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120).

Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982).

Antibody fragments can be obtained using methods well known in the art (see, for example, Harlow & Lane, 1988, "*Antibodies: A Laboratory Manual*", Cold Spring Harbor Laboratory, New York). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

It will be appreciated by persons skilled in the art that for human therapy or diagnostics, human or humanised antibodies are preferably used. Humanised forms of non-human (e.g. murine) antibodies are genetically engineered chimaeric antibodies or antibody fragments having preferably minimal-portions derived from non-human antibodies. Humanised antibodies include antibodies in which complementary determining regions of a human antibody (recipient antibody) are replaced by residues from a complementary determining region of a non-human species (donor antibody) such as mouse, rat of rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. *Nature* 321:522-525; Riechmann et al., 1988, *Nature* 332:323-329; Presta, 1992, *Curr. Op. Struct. Biol.* 2:593-596).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, *Nature* 321:522-525; Reichmann et al., 1988. *Nature* 332:323-327; Verhoeyen et al., 1988, *Science* 239: 1534-15361; U.S. Pat. No. 4,816,567) by substituting human complementarity determining regions with corresponding rodent complementarity determining regions. Accordingly, such humanised antibodies are chimaeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Carlsson & Söderlind, 2001, *Expert Rev Mol. Diagn.* 1(1):102-8; Hoogenboom & Winter, 1991, *J. Mol. Biol.* 227:381; Marks et al., 1991, *J. Mol. Biol.* 222:581; Cole et al., 1985, In: *Monoclonal antibodies and Cancer Therapy*, Alan R. Liss, pp. 77; Boerner et al., 1991. *J. Immunol.* 147:86-95).

Once suitable antibodies are obtained, they may be tested for activity, for example by ELISA.

Thus, in one embodiment, the polypeptide may be an intact antibody (such as an IgG molecule).

Alternatively, the polypeptide may be an antigen-binding fragment of such an antibody.

In one embodiment, the antibody is a recombinant antibody.

In a further embodiment, the antibody is a monoclonal antibody.

The antibodies, or antigen-binding fragment thereof, may target any antigen known to have a modulatory role in the immune system. Preferably, however, wherein the antibody, or antigen-binding fragment thereof, is capable of binding specifically to an antigen selected from the group consisting of CD40, CD137, OX-40 and receptors thereof.

In one preferred embodiment, the antibody, or antigen-binding fragment thereof, is capable of binding specifically to CD40 (such as human CD40, e.g. see NCBI Reference Sequence: NP_001241.1).

CD40 comprises four extracellular domains (designated D1, D2, D3 and D4), each of which is subdivided into an A-module and a B-module (see Naismith et al. Modularity in the TNF-receptor family. *Trends in Biochem. Sci* 1998, 23:74-79). In one embodiment, the antibody, or antigen-binding fragment thereof, is capable of binding specifically to module B2 of domain 1 of CD40 (or an epitope comprising the same).

Suitable antibodies, as well as antigen-binding fragments and variant thereof, are described in Ellmark et al. Modulation of the CD40-CD40 ligand interaction etc 2002 *Immunology* 106:456-463.

In a further preferred embodiment on the compositions of the invention, the immunostimulatory polypeptide is a CD40 agonist (i.e. the polypeptide activates, at least partially, the CD40 receptor). Polypeptide with CD40 agonist properties may be identified using methods well known in the art, for example as described in Pound J D *Int Immunel* 1999; 11(1):11-20, Ledbetter et al, *Critical Reviews in Immunology* 1997, Ellmark et al 2002 Immunology.

Suitable CD40 agonists include, but are not limited to, CD40L (such as Avrend™ [Immunex Corp]), anti-CD40 antibodies and antigen-binding fragment and variants of the same (such as CP-870-893 [Pfizer] and SGN-40 [Seattle Genetics/Genentech]).

In a further preferred embodiment, the polypeptide is capable of activating T-cells directly via CD40 and/or indirectly via activation of dendritic cells via CD40 and/or is capable of a direct apoptotic effect on CD40-expressing tumor cells.

A second essential component of the compositions of the invention is PGA nanoparticles.

In one embodiment, the PGA may be selected from the group consisting of γ-PGA, α-PGA, water soluble salts of PGA, and metal salts of PGA.

Thus, in one embodiment, the nanoparticles comprise or consist of γPGA.

Biodegradable γPGA nanoparticles are believed to provide several advantages, including to a favourable size in the nano-scale range, a favourable release profile of adsorbed antibody, and a favourable biodistribution[44] (arising from the nanoparticle size). The γ-PGA nanoparticles have a unique release profile due to the nature of the nanoparticles and the type of specificity of the immunostimulatory polypeptides (e.g. antibodies) adsorbed to their surface, which may provide an enhanced effect in cancer treatment. Another factor that may affect the biodistribution of particles in the nanoscale is that they are in the same size range as viruses. Antigen-presenting cells (APCs, e.g. B cells, macrophages and dendritic cells) are particularly effective in taking up and processing particles in this size[46,47]. This may prove an advantage when targeting APCs, by providing a stimulatory signal to the appropriate cells, thus promoting uptake and degradation of the nanoparticles. The small size of the nanoparticles also increases the surface to mass ratio, compared to particles in the microscale, which allows for more effective adsorption of immunostimulatory polypeptides.

In a further embodiment, the nanoparticle further comprises a hydrophobic amino acid, or an ester thereof. For example, the hydrophobic amino acid may be phenylalanine.

Thus, the nanoparticles may comprise or consist of phenylalanine ethyl ester conjugated onto a γPGA chain.

In one preferred embodiment, the nanoparticles are biodegradable.

It will be appreciated by persons skilled in the art that the nanoparticles may be of uniform or variable size.

In one embodiment, the nanoparticles have a mean particle diameter of 25 to 500 nm, for example of 100 nm to 300 nm. For example, the nanoparticles may have a mean particle diameter of 200 nm.

In a further embodiment, the nanoparticles have a negative surface charge. For example, the negative surface charge may be between −10 mV and −35 mV, for example about −15 mV.

In a still further embodiment, the nanoparticles are capable of binding to toll-like receptors (TLRs), such as TLR-2 and/or TLR-4.

Persons skilled in the art will appreciate that the above described embodiments of the two essential components of the invention may be combined in any combination.

Thus, in one embodiment, the composition of the first aspect of the invention may comprise a mixture of:
  (a) a CD40 agonist; and
  (b) γPGA nanoparticles.

For example, the composition may comprise:
  (a) an anti-CD40 antibody or antigen-binding fragment thereof; and
  (b) nanoparticles comprising or consisting of phenylalanine ethyl ester conjugated to γPGA.

In one such preferred composition, the nanoparticles have a mean particle diameter of 200+/−50 nm.

It will be further appreciate by skilled persons that the compositions of the invention may comprise additional components.

Thus, in one embodiment, the composition may comprise a second immunostimulatory polypeptide. Thus, the composition may comprise combinations of such polypeptides, for example two or more of the following:
  CD137 antibodies, CD40 antibodies and OX-40 antibodies.

In a further embodiment, the composition may comprise an antigen. Thus, the composition may comprise a cancer cell antigen.

The compositions of the invention may be suitable for administration by any known route, including topical, local and systemic.

The active components of the compositions of the invention can be formulated at various concentrations, depending on the efficacy/toxicity of the polypeptide/nanoparticles being used and the indication for which it is being used. For example, the composition may comprise the polypeptide component at a concentration of between 0.1 µM and 1 mM, more preferably between 1 µM and 100 µM, between 5 µM and 50 µM, between 10 µM and 50 µM, between 20 µM and 40 µM and most preferably about 30 µM.

It will be appreciated by persons skilled in the art that the active components will generally be administered in admixture with a suitable pharmaceutical excipient diluent or carrier selected with regard to the intended route of administration and standard pharmaceutical practice (for example, see Remington: The Science and Practice of Pharmacy, 19$^{th}$ edition, 1995, Ed. Alfonso Gennaro, Mack Publishing Company, Pennsylvania, USA). For example, the composition may be formulated so as to be suitable for administration parenterally, topically, orally, by inhalation and in the form of a suppository or pessary.

Thus, in one embodiment, the composition is for administration parenterally, for example locally into or near a tumor (such as intratumorally, intraperitumorally, peritumorally, intranodally), intravenously, intramuscularly, subcutaneously, intrathecally, intracerebrally and/or intracerebroventricularly, or they may be administered by infusion techniques. Such compositions are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

The compositions of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or 'puff' contains at least 1 mg of a compound of the invention for delivery to the patient. It will be appreciated that the overall daily dose with an aerosol will vary from patient to patient, and may be administered in a single dose or, more usually, in divided doses throughout the day.

Alternatively, the compositions of the invention can be administered in the form of a suppository or pessary, or they may be applied topically in the form of a lotion, solution, cream, ointment or dusting powder. The compositions of the invention may also be transdermally administered, for example, by the use of a skin patch. They may also be administered by the ocular route.

For ophthalmic use, the agents of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compositions of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

In one particular embodiment, the composition is formulated as a sustained-release drug delivery system.

Alternatively, the compositions of the present invention can be administered by a surgically implanted device that releases the drug directly to the required site.

A second aspect of the invention provides a composition as described above for use in medicine.

A third aspect of the invention provides a composition as described above for use in stimulating the immune system of a patient.

In one embodiment, the composition is for use in the treatment of cancer.

For example, the cancer may be selected from the group consisting of lymphomas, melanomas, hepatomas, osteosarcomas, renal cell carcinomas, bladder carcinomas, breast cancers, colorectal carcinomas, lung cancer, gastrointestinal cancer, pancreatic cancer, prostate cancer, ovarian cancer, kidney cancer and leukemia.

By 'treatment' we include both therapeutic and prophylactic treatment of the patient. The term 'prophylactic' is used to encompass the use of a polypeptide or formulation described herein which either prevents or reduces the likelihood of cancer in a patient or subject.

It will be appreciated by persons skilled in the art that the compositions may be for use in combination with one or more conventional anticancer therapies, such as chemotherapy, radiotherapy and/or surgery.

In another embodiment, the composition is for use in the treatment of viral infection (for example, HIV/AIDS).

In a further embodiment, the composition is for use in the treatment of autoimmune disease.

A related fourth aspect of the invention provides the use of a composition according to the first aspect of the invention in the preparation of a medicament for stimulating the immune system of a patient.

In one embodiment, the medicament is for use in the treatment of cancer.

For example, the cancer may be selected from the group consisting of lymphomas, melanomas, hepatomas, osteosarcomas, renal cell carcinomas, bladder carcinomas, breast cancers, colorectal carcinomas, lung cancer, gastrointestinal cancer, pancreatic cancer, prostate cancer, ovarian cancer, kidney cancer and leukemia.

It will be appreciated by persons skilled in the art that the medicament may be for use in combination with one or more conventional anticancer therapies, such as chemotherapy, radiotherapy and/or surgery.

In another embodiment, the medicament is for use in the treatment of viral infection (for example, HIV/AIDS).

In a further embodiment, the medicament is for use in the treatment of autoimmune disease.

A fifth aspect of the invention provides a method for stimulating the immune system in a subject comprising administering to the subject a composition according to the first aspect of the invention.

In one embodiment, the method is for treating cancer in a subject (as discussed above).

In another embodiment, the method is for treating a viral infection in a subject (as discussed above).

In a further embodiment, the method is for treating an autoimmune disease in a subject (as discussed above).

It will be appreciated by skilled persons that the composition may be administered to the subject by any of the routes known in the art. Thus, the compositions may be administered to the subject parenterally locally into or near a tumor (such as intratumorally, intraperitumorally, peritumorally, intranodally), intravenously, intramuscularly, subcutaneously, intrathecally, intracerebrally and/or intracerebroventricularly.

In one embodiment of the uses and methods of the invention, the composition is for local administration at or near a site where immune stimulation would be beneficial to a patient. Such use provides for enhanced local stimulation of the immune system (e.g. in and around a tumor), including the release of TH1-type cytokines. At the same time, the compositions of the invention may provide reduced systemic immune stimulation, for example reducing the adverse effects associated with 'global' release of cytokines into the body (such as liver damage).

A sixth aspect of the invention provides a kit of parts comprising:
(a) an immunostimulatory polypeptide; and
(b) nanoparticles.

In one embodiment, components (a) and (b) are formulated separately in a pharmaceutically-acceptable excipient, diluent or carrier.

The components (a) and (b) may be each provided in a form that is suitable for administration in conjunction with the other.

By the term "administration in conjunction with" we include that the two components of the kit (the immunostimulatory polypeptide and the nanoparticles) are administered (optionally repeatedly), either together, or sufficiently closely in time, to enable a beneficial effect for the patient, that is greater, over the course of the treatment of the relevant condition, than if either a formulation comprising the immunostimulatory polypeptide, or a formulation comprising the nanoparticles, are administered (optionally repeatedly) alone, in the absence of the other component, over the same course of treatment. Determination of whether a combination provides a greater beneficial effect in respect of, and over the course of treatment of, a particular condition will depend upon the condition to be treated or prevented, but may be achieved routinely by the skilled person.

In another embodiment, components (a) and/or (b) are freeze-dried.

In a further embodiment, components (a) and (b) are each provided in a sealed, sterile container.

It will be appreciated by skilled persons that component (a) may be as defined above in relation to the first aspect of the invention. Likewise, component (b) may be as defined above in relation to the first aspect of the invention.

The kits of the invention may further comprise instructions for performing a method according to the fifth aspect of the invention.

A seventh aspect of the invention provides an immunostimulatory polypeptide for use in medicine in combination with nanoparticles, wherein the nanoparticles comprise or consist of polyglutamic acid (PGA).

In one embodiment, the immunostimulatory polypeptide is as defined above in relation to the first aspect of the invention.

Thus, the immunostimulatory polypeptide may a CD40 agonist, such as an anti-CD40 antibody or antigen-binding fragment thereof.

In another embodiment, the immunostimulatory polypeptide is for use in medicine in combination with γPGA nanoparticles.

In a further embodiment, the immunostimulatory polypeptide is for use in the treatment of cancer.

The immunostimulatory polypeptide may be for administration parenterally, for example locally into or near a tumor (such as intratumorally, intraperitumorally, peritumorally, intranodally), intravenously, intramuscularly, subcutaneously, intrathecally, intracerebrally and/or intracerebroventricularly.

An eighth aspect of the invention provides nanoparticles for use in medicine in combination with an immunostimulatory polypeptide, wherein the nanoparticles comprise or consist of polyglutamic acid (PGA).

In one embodiment, the nanoparticles are as defined above in relation to the first aspect of the invention.

Thus, the nanoparticles may comprise or consist of γPGA. For example, the nanoparticles may comprise or consist of phenylalanine ethyl ester conjugated to γPGA.

In another embodiment, the nanoparticles are for use in medicine in combination with a CD40 agonist, such as an anti-CD40 antibody or antigen-binding fragment thereof.

In a further embodiment, the nanoparticles are for use in the treatment of cancer.

The nanoparticles may be for administration parenterally, for example locally into or near a tumor (such as intratumorally, intraperitumorally, peritumorally, intranodally), intravenously, intramuscularly, subcutaneously, intrathecally, intracerebrally and/or intracerebroventricularly.

A ninth aspect of the invention provides a method for producing a pharmaceutical composition according to the first aspect of the invention comprising admixing an immunostimulatory polypeptide and nanoparticles together with a pharmaceutically acceptable diluent, carrier or excipient.

Preferred, non-limiting examples which embody certain aspects of the invention will now be described, with reference to the following figures:

FIG. 1

Mixtures of γ-PGA nanoparticles and anti-CD40 antibodies have a strong synergistic effect on CD40-induced B cell proliferation. Human CD19+ B-cells from blood were cultured for 72 h with different concentrations of anti-CD40 antibodies in the absence or presence of 100 µg/ml γ-PGA nanoparticles. Untreated cells or cells treated with γ-PGA nanoparticles alone were used as controls. Proliferation was assayed by [3H]thymidine incorporation. Data represent stimulation index (SI) based on CPM-values+/−SEM, where the untreated control represents SI=1, n=3 donors.

FIG. 2

Comparison of B cell proliferation induced by stimulation with anti-CD40 antibodies immobilized onto or in mixture with γ-PGA nanoparticles. Human blood CD19+ B-cells were cultured for 72 h with different concentrations of anti-CD40 antibodies alone, immobilized (imm) or in mixture with γ-PGA nanoparticles. Untreated cells and cells stimulated with corresponding concentrations of γ-PGA nanoparticles present in the stimulations with immobilized/mixed CD40-antibodies were used as controls. Proliferation was assayed by [3H]thymidine incorporation. Data represent stimulation index (SI) based on CPM-values+/−SEM, where the untreated control represents SI=1, n=3 donors.

FIG. 3

B cell proliferation in response to stimulation with anti-CD40 antibodies encapsulated in γ-PGA nanoparticles. Human blood CD19+ B-cells were cultured for 72 h with different concentrations of free or encapsulated (ecp) anti-CD40 antibodies. Untreated cells and cells stimulated with corresponding concentrations of γ-PGA nanoparticles present in the stimulations with encapsulated CD40-antibodies were used as controls. Proliferation was assayed by [3H] thymidine incorporation. Data represent stimulation index (SI) based on CPM-values+/−SEM, where the untreated control represents SI=1, n=3 donors.

FIG. 4

Murine spleen CD19+ B-cells were cultured for 72 h with different concentrations of anti-CD40 antibodies (FGK-45) in the absence or presence of 100 µg/ml γ-PGA nanoparticles. Untreated cells or cells treated with γ-PGA nanoparticles alone were used as controls. Proliferation was assayed by [3H]thymidine incorporation. Data represent stimulation index (SI) based on CPM-values+/−SEM, where the untreated control represents SI=1, n=2 spleens.

FIG. 5

Blocking of TLR2 or TLR4 on Monocyte-derived dendritic cells decrease the stimulatory effect of γ-PGA NPs. Immature Monocyte-derived dendritic cells were incubated with 20 µg/ml TLR2 or TLR4 neutralizing Abs for 1 h and thereafter stimulated for 48 h with 100 µg/ml γ-PGA NPs. Alterations in expression levels of HLA-DR, CD86 and CD80 were analyzed with flow cytometry. C denotes untreated control. Mean fluorescence intensity (MFI)±SEM is shown, n=5. The statistical significance was determined by paired Student's two-tailed t-test (*=p<0.05, **=p<0.01).

FIG. 6

CD40 antibodies are adsorbed on the surface of γ-PGA nanoparticles. A mixture of γ-PGA nanoparticles (100 µg/ml) and anti-CD40 antibodies (B44, 4.3 µg/ml) were incubated for 15 min at 4° C. and subsequently washed three times by centrifugation. Human CD19+ B-cells were stimulated for 72 h with a fresh mix of γ-PGA nanoparticles and anti-CD40 antibodies (wash 0) or the anti-CD40 antibody/γ-PGA nanoparticle mix retrieved after wash 1, 2 or 3. Untreated cells or cells treated with γ-PGA nanoparticles or anti-CD40 antibodies alone were used as controls. Proliferation was assayed by [3H]thymidine incorporation. Data represents stimulation index (SI) based on CPM-values+/−SD, were the untreated control represents SI=0, n=2 donors.

FIG. 7

Comparison of different polymer-based nanoparticles. Human CD19+ B-cells were incubated for 72 h with 100 µg/ml of γ-PGA or polylactide nanoparticles, with or without anti-CD40 antibodies (4.3 µg/ml). Proliferation was assayed by [3H]thymidine incorporation. Data represents stimulation index (SI) based on CPM-values+/−SD, were the untreated control represents SI=0, n=4 donors.

FIG. 8

The nanoparticle compositions of the invention prevent the release of cytokines typically associated with systemic administration of a CD40 agonist. In a subcutaneous MB49 (bladder cancer) tumor in C57BL/6 mice, cytokine release was studied following treatment with anti-CD40 antibody, anti-CD40 antibody mixed with γ-PGA nanoparticles, or isotype control antibody mixed with γ-PGA nanoparticles. Serum samples, were taken 4 hours post treatment, and levels of IL6, IL10, and TNF-α were analysed. Students T-test indicates statistical significance for FGDK45 versus FGK45 mixed with γ-PGA nanoparticles for IL6 day 22 p<0.05, 100 day 15, p<0.00004, TNFα day 8 p<0.02, day 22 p<0.03.

EXAMPLES

Example 1

Synergistic Activation of CD40 by a Mixture of γ-PGA Nanoparticles and Anti-CD40 Antibodies Introduction The invention provides drug formulations composed of nanoparticles and protein drugs that significantly increase their therapeutic effect. The formulations have the potential to increase agonistic properties, increase the cross linking of protein drugs targeting immunoregulatory molecules, increase the duration and tissue retention of the drug. They have furthermore the potential to function as controlled release vehicle and reduce the dosing frequency and thereby increased patient convenience and reducing the risk of systemic leakage and thus systemic side effects. The described synergistic effect is demonstrated herein on the CD40, but also extends to other immunoregulatory and other cell receptors, as well as combinations of receptors. The invention thus provides significant benefits to treatment of cancer (immunotherapy), vaccination (cancer, virus etc) as well as HIV/AIDS therapy.

Materials & Methods

Human CD19-positive B-cells were isolated from peripheral blood (Lund University Hospital, Lund, Sweden) using human CD19 magnetic microbeads (Miltenyi Biotech, Bergisch Gladbach, Germany). Cells were cultured in 96-well plates (150.000 cells/well) in RPMI 1640 medium (Invitrogen, Carlsbad, Calif., USA) supplemented with 2 mM L-glutamine and 50 µg/ml gentamicin (Sigma-Aldrich, St. Louis, Mo., USA) and 10% (v/v) heat inactivated foetal bovine serum (Invitrogen). 3H-thymidine (0.0185 MBq/well or 0.5 µCi/well) was purchased from Perkin Elmer (Waltham, Mass., USA). Samples were run in five replicates and 3H-thymidine incorporation was measured in a beta scintillation counter (Matrix 96 Direct beta counter, Packard, Meriden, Conn.).

Figure 2:
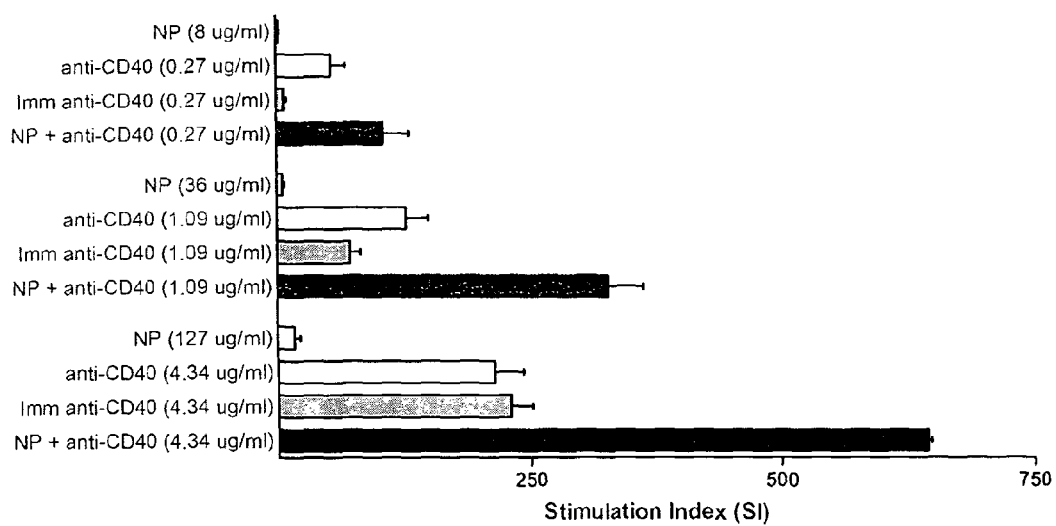

The amphiphilic γ-PGA particles used was synthesized by conjugating hydrophobic amino acids, (phenylalanine) onto the γ-PGA chain, creating a γ-PGA hydrophobic derivative (γ-hPGA). Pre-made γ-hPGA nanoparticles with 53% of L-Phe grafting degree with a diameter of approximately 200 nm (provided by Prof. Akashi; see also EP 1 932 538 A) were used for the mixing and immobilization experiments (FIGS. 1 and 2). For the nanoparticles with encapsulated protein drug (FIG. 3), crude (γ-hPGA) was used.

Mixing of CD40 Antibody and Nanoparticles

The nanoparticles were mixed with the anti-CD40 antibody prior to addition of this mixture to the cell culture.

Immobilization

A carboxyl group of the γ-hPGA nanoparticles (10 mg/ml in phosphate buffer, pH 5.8) was first activated by 1-ethyl-3-(3-dimethylaminopropyl)carbodiimide (WSC) (1 mg/ml) for 20 min. The nanoparticles (5 mg) obtained by centrifugation (14,000×g for 15 min) were then mixed with 1 ml of protein (1.75 mg/ml) in phosphate-buffered saline (PBS, pH 7.4), and the mixture was incubated at 4° C. for 24 h. After the reaction was terminated, the nanoparticles were isolated by centrifugation, washed twice with PBS or water, and resuspended at 10 mg/ml in PBS. Protein-encapsulated nanoparticles were added to the same volume of 4% sodium dodecyl sulfate (SDS) to dissolve the nanoparticles, and the protein loading content was then determined by the Lowry method.

Encapsulation

To prepare the protein-encapsulated γ-hPGA nanoparticles, 0.25-4 mg of protein (Ab) was dissolved in 1 ml of saline, and 1 ml of the γ-hPGA (10 mg/ml in DMSO) was added to the protein solution. The resulting solution containing nanoparticles encapsulating the Ab was centrifuged at 14,000×g for 15 min, and repeatedly rinsed. The protein loading content was measured by the Lowry method. Protein-encapsulated nanoparticles were added to the same volume of 4% sodium dodecyl sulfate (SDS) to dissolve the nanoparticles, and the protein loading content was then determined by the Lowry method.

B-Cell Proliferation Assay

Human CD19+ B-cells were cultured for 72 h with anti-CD40 antibody (0.07, 0.27, 1.08 or 4.33 µg/ml) with or without 100 µg/ml of γ-PGA nanoparticles, or with 100 µg/ml of γ-PGA nanoparticles alone. Encapsulated and immobilized anti-CD40 antibodies were added to B cells at identical concentrations (based on anti-body concentration). Untreated cells were used as control. 3H-thymidine was added during the last 16 h of incubation in order to assess proliferation. Stimulation index (SI) values were calculated according to the formula: [CPM (counts per minute) of treated cells—CPM of untreated cells]/CPM of untreated cells. Data were obtained from three separate experiments on different donors, and values were scaled according to a calculated normalization factor.

Murine CD19+ B-cells were cultured for 72 h with anti-CD40 antibody (0.07, 0.27, 1.08 or 4.33 µg/ml) with or without 100 µg/ml of γ-PGA nanoparticles, or with 100 µg/ml of γ-PGA nanoparticles alone.

Results

As shown in FIG. 1, it was found that a mixture of γ-PGA nanoparticles and anti-CD40 antibodies have a strong synergistic effect on CD40 activation, as demonstrated by B cell proliferation. These results were consistent at each antibody concentration. CD40 antibodies alone and nanoparticles alone have, even when stimulation signals are added, a much lower activation efficacy than the mixture of the nanoparticles and the anti-CD40 antibody.

Figure 3:
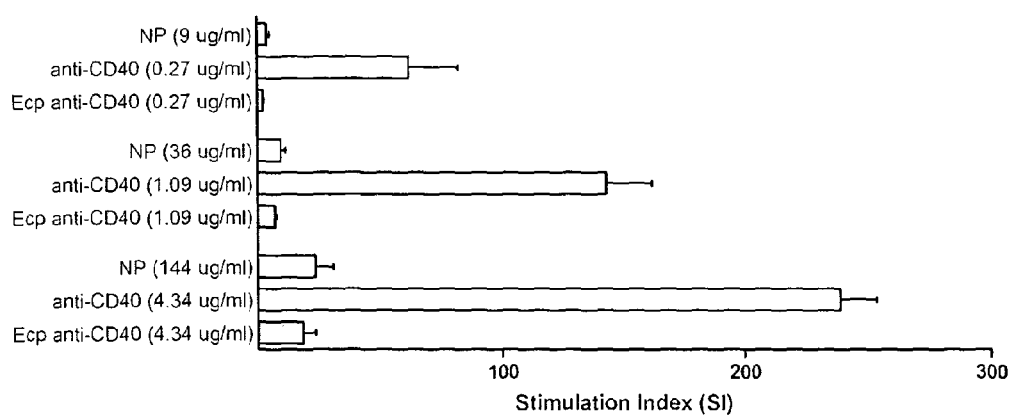
Figure 4:
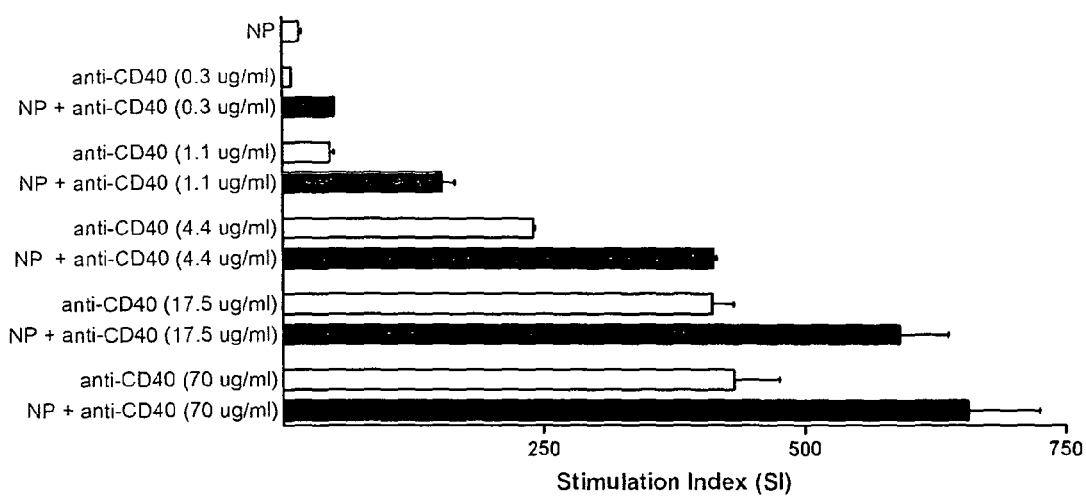

No such effect was seen when the nanoparticles were immobilized covalently (FIG. 2) or when the anti-CD40 antibodies was encapsulated in the nanoparticles (FIG. 3).

Figure 5:
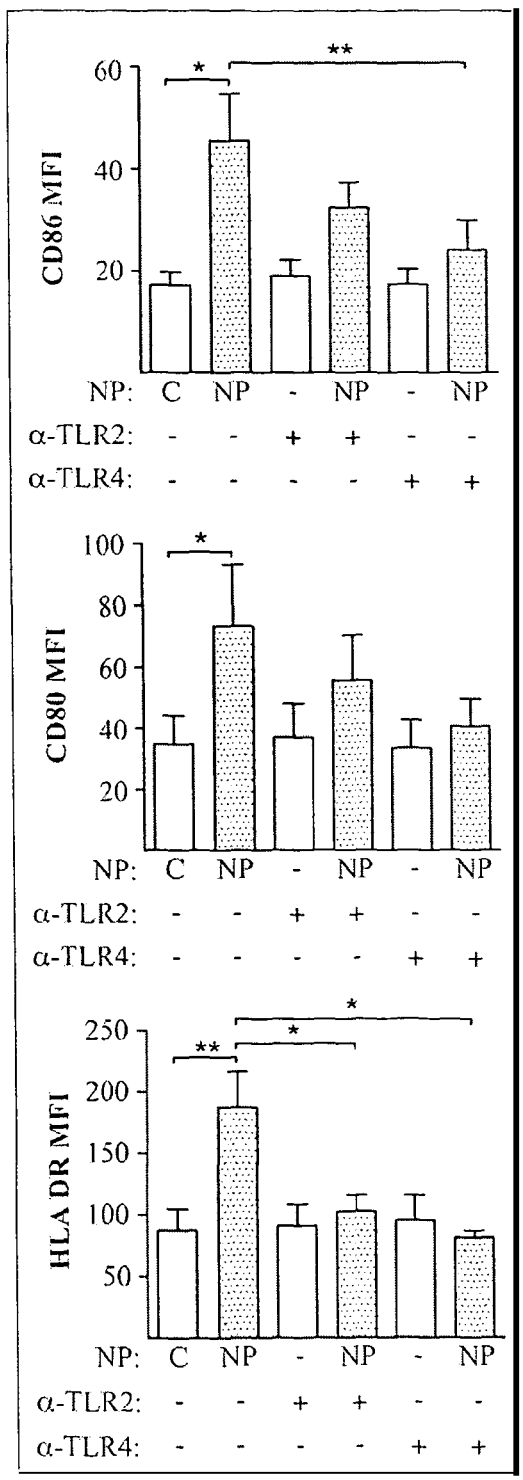

As can be seen in FIG. 5, the γ-PGA nanoparticles have a small immunostimulatory effect on their own. Antibodies that bind to and block TLR-2/4 significantly decrease this immunostimulatory effect of the γ-PGA nanoparticles on moDc. Thus, it would appear that the nanoparticles may bind to TLR-2/4 and that this is interaction may underlie (at least in part) the synergistic effect shown in FIG. 1.

Discussion

It has been shown that the minimal requirement to induce a signal through CD40 is the formation of a receptor dimer[11] and that the strength of the receptor mediated signal correlates with increasing valency of an extracellularly applied ligand[12]. Intracellular signal transmission through CD40 depends on adapter molecules (most notably the TNFR associated factor (TRAF) family) that interacts with different intracellular recognition motifs[14;15;35]. Extracellular cross-linking of CD40 leads to a stabilization of these intracellular adaptor molecules, which in turn initiate the signalling cascade. The more the receptor is cross-linked, the more/larger and more stable signalling complex is generated. It may thus be hypothesized that the synergistic signalling effect, significantly higher than for the CD40 antibody alone or the nanoparticles alone, seen in FIG. 1, is due to a higher order of CD40 cross linking. It has been demonstrated that proteins can be adsorbed to these nanoparticles very effectively[36]. Adsorbed to the nanoparticles, the CD40 antibodies have the potential to cross link multiple (more than two) CD40s.

Unexpectedly, the nanoparticles with CD40 Ab immobilized to the surface (FIG. 2) did not provide a similar synergistic effect. Although they did induce CD40 activation it was not higher than for the CD40 antibody alone. Encapsulation of the CD40 antibody demonstrated even lower activation efficacy (FIG. 3).

The formulation described in this Example thus displays a unique strongly synergistic CD40 activating effect, which is indicative of a significant therapeutic effect in cancer treatment (bladder, melanoma breast, colorectal, stomach, pancreas etc), but also indicative of an adjuvant effect in several types of vaccination formulations against (cancer, viruses parasites, bacteria, etc). In addition, such an CD40 activating effect is indicative of a therapeutic effect in HIV/AIDS-treatment[42].

In addition to the increased anti-CD40 activation efficacy the described, the compositions of the invention may increase the function of protein drugs targeting immunoregulatory molecules by improving the efficacy due to increased duration and tissue retention of the drug, reducing the dosing frequency and thereby increased patient convenience and reducing the risk of systemic leakage and thus systemic side effects.

Example 2

Anti-CD40 Antibodies are Adsorbed on to the Surface of γ-PGA Nanoparticles

Materials & Methods

In order to investigate the extent to which freely mixed CD40 antibodies are adsorbed on the surface of γ-PGA nanoparticles, a mixture of γ-PGA nanoparticles (100 µg/ml) and anti-CD40 antibodies (B44, 4.3 µg/ml) was incubated for 15 min at 4° C. The mixture was then centrifuged at 13000 rpm for 10 min and the supernatant removed. The remaining pellet was resuspended to a fixed nanoparticle concentration and a sample was withdrawn.

This procedure was then repeated twice for a total of three washes.

Proliferation was assessed on human CD19+ B-cells stimulated for 72 h with a fresh mix of γ-PGA nanoparticles and anti-CD40 antibodies (wash 0) or the anti-CD40 antibody/γ-PGA nanoparticle mix retrieved after wash 1, 2 or 3. Data were obtained from two separate experiments on different donors, and values were scaled according to a calculated normalization factor.

Results

Figure 6:
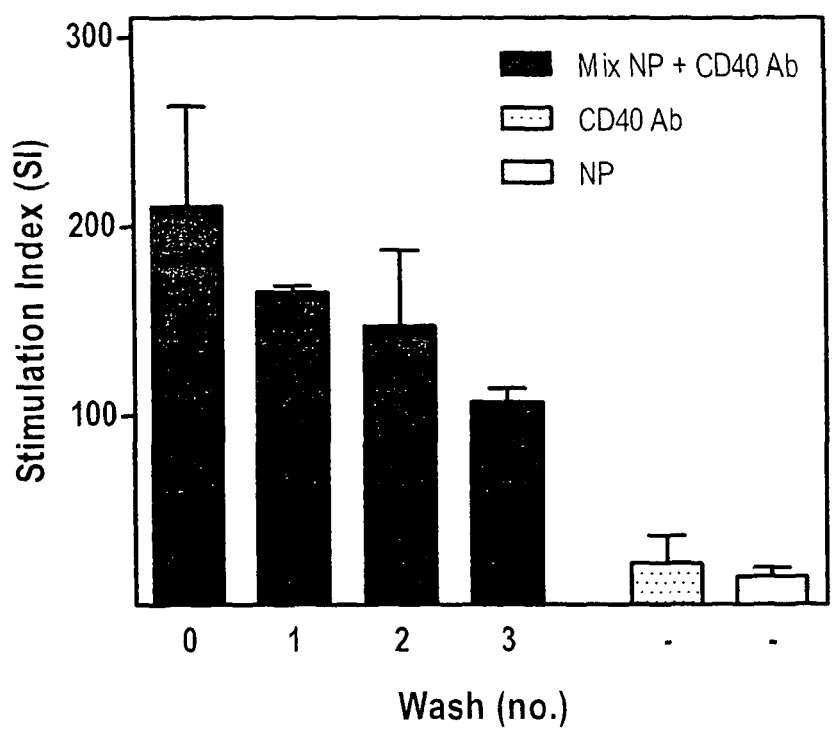

Results from the adsorption assay studies are shown in FIG. 6.

The data demonstrate that the exemplary CD40 antibody/γ-PGA nanoparticle composition of the invention retains its synergistic effect on B cell stimulation after washing steps are performed. After a third round of washing performed on γ-PGA nanoparticle composition the observed synergistic effect is lowered by 50% compared to the observed effect without including washing. Thus, adsorption, or association, of the CD40 antibody onto the γ-PGA nanoparticles in the composition of the present invention, is achieved.

Example 3

Comparison of Different Nanoparticles

Materials & Methods

Human CD19+ B-cells were cultured with 100 µg/ml of γ-PGA nanoparticles or plain polylactide nanoparticles (250 nm size, Corpuscular Inc., Cold Spring, N.Y., USA), with or without anti-CD40 antibodies (4.3 µg/ml). Untreated cells were used as control and proliferation was assayed after 72 h. Data were obtained from four separate experiments on different donors and values were scaled according to a calculated normalization factor.

Results

Figure 7:
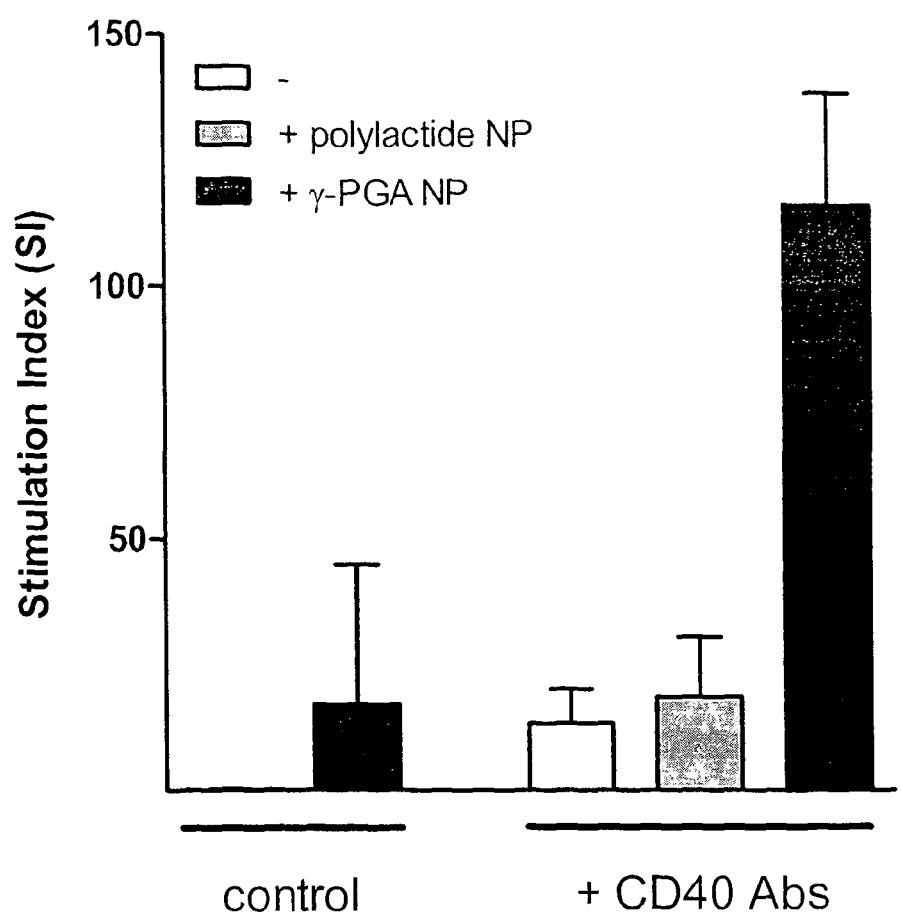

Results from the nanoparticle comparison studies are shown in FIG. 7.

The unexpected synergistic effect on B cell stimulation demonstrated in Example 1 for the exemplary γPGA nanoparticle composition of the invention was not observed for a nanoparticle composition comprising plain polylactide nanoparticles mixed with an anti-CD40 antibody (using the mixing protocol described in Example 1 above).

PLGA and PLA micro-particles (Poly(lactide-co-glycolide) and poly(lactide acid)) are other types of biodegradable material commonly used in nanoparticle formulations. However, problems have been reported in relation to nanoparticle formulations based on these materials. For example, low encapsulation efficiency of hydrophilic proteins, and instability of the protein and nanoparticle composition during formulation, storage, and lyophilization[36,44]. In addition, the production of nanoparticles using PLGA material typically involve organic solvents, which may affect the stability, integrity and function of the protein component of the composition.

The γPGA nanoparticle-based compositions of the present invention do not suffer from such limitations.

Example 4

Reduction in Cytokine Release In Vivo Following Anti-CD40 Antibody Administration in γ-PGA Nanoparticles Materials & Methods $3 \times 10^5$ MB9 cells (bladder cancer) are inoculated subcutaneously (s.c.) in leg of female C57BL/6 mice (Taconic Denmark) on day 0.

Anti-CD40 antibody, FGK-45 (BioXCell BE0016-2,), Rat-IgG2a, or isotype control 2A3 (BioXcell BE0089), and γ-PGA nanoparticles were mixed and prepared according to the mixing protocol.

Group 1 (10 mice) were peritumorally administered with isotype control adsorbed to γ-PGA nanoparticles on day 8, 15 and 22 (diamonds).

Group 2 (10 mice) were peritumorally administered with 10 µg FGK-45 on day 8, 15 and 22 (squares).

Group 3 (10 mice) were peritumorally administered with 10 µg FGK-45 adsorbed to γ-PGA nanoparticles on day 8, 15 and 22 (triangles).

Serum samples, were taken 4 hours post each treatment, and cytokine levels were analysed using cytokine beads array (BD™ CBA Mouse inflammation kit instruction manual" Cat No 552364. BD Biosciences). Theoretical limit of detection: IL-6 5 pg/ml, IL-10 17.5 pg/ml, TNF 7.3 pg/ml.

Results

Figure 8:
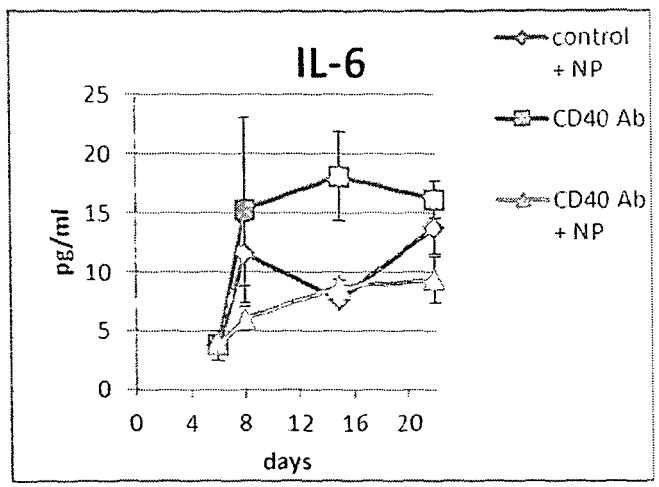
Figure 8:
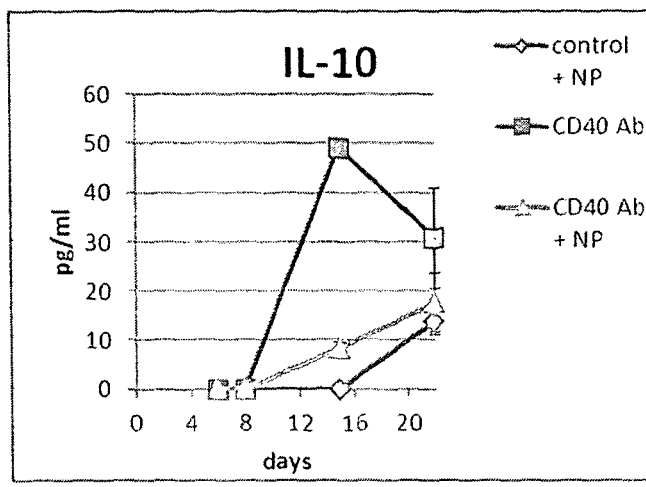
Figure 8:
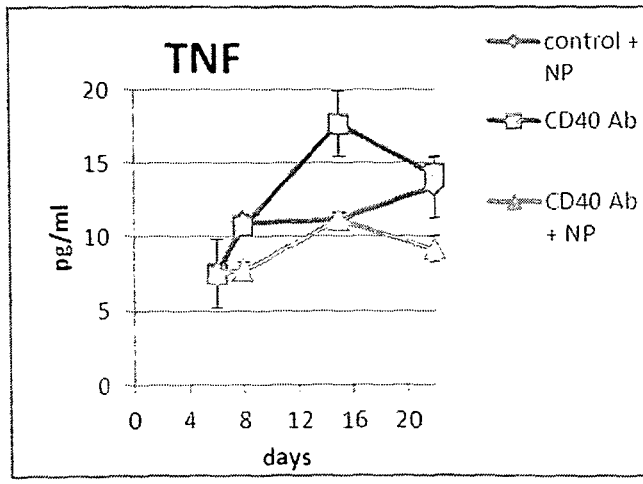

Results from this study are shown in FIG. 8.

Tumor-bearing mice treated with mixture anti-CD40 antibody and γ-PGA nanoparticles have lowered cytokine concentrations of IL6, IL10, and TNFα in serum compared to tumor-bearing mice treated with anti-CD40 antibody.

Treatment with a systemic CD40 agonist is associated with cytokine release syndrome[33,34], and thus characterized by release of cytokines, such as TNFalpha and IL-6[48]. Elevation of cytokine levels is associated with liver damage, and elevation of biomarkers such as alanine aminotransferase (ALAT) and aspartate aminotransferase (ASAT)[33,34,49]. The results presented herein demonstrate that the compositions and methods of the invention produce lowered serum levels of IL-6, IL-10, and TNF-alpha, indicative of the potential to minimize toxic side effects (such as liver damage) associated with systemic release of CD40 agonist antibodies.

Furthermore, the serum levels were also lowered for the cytokines IL-12, IFN-gamma, and MCP-1, following the treatment with the composition of the present invention, in comparison to treatment with an anti-CD40 antibody.

Conclusion

Thus, the data presented herein demonstrate that the nanoparticle compositions of the invention are capable not only of enhancing synergistically the immunostimulatory effect induced by anti-CD40 antibodies locally at the site of administration (e.g. in and around a tumor) but also serve to minimise adverse systemic immune stimulation typically associated with such antibodies (which can lead to liver toxicity).

Example 5

In Vivo Experimental Design for Cancer Therapy $2.5 \times 10^5$ tumor cells (e.g. Panc02 cells) or $3 \times 10^5$ MB49 cells are inoculated subcutaneously (s.c.) in the right hind leg of female C57BL/6 mice on day 0.100 µl of anti-CD40 antibody (FGK-45) stock solution/dose mixed and/or adsorbed on γ-PGA nanoparticles is administered three or six times with a three-day interval intratumorally and or peritumorally. Therapy is started on day 5 after tumor injection for the Panc02 model and on day 8 for the MB49 model.

Tumor growth and survival is monitored throughout the experiment. Tumor volume is measured with calipers and calculated by the ellipsoid volume formula: $=4/3 * \pi * a$ (length)*b(width)*c(depth). The pharmacokinetics of the antibody, known biomarkers (e.g. IL-6, TNF-alpha, IFN-gamma) for immune activation, as well as markers for hepatotoxicity (ASAT and ALAT) may be followed in the mice.

The mice are followed for up to 70 days.

REFERENCES

1. Schonbeck U, Libby P. The CD40/CD154 receptor/ligand dyad. Cell Mol Life Sci 2001; 58(1):4-43
2. van Kooten C, Banchereau J. CD40-CD40 ligand. J Leukoc Biol 2000; 67(1):2-17.
3. Quezada S A, Jarvinen L Z, Lind E F, Noelle R J. CD40/CD154 interactions at the interface of tolerance and immunity. Annu Rev Immunol 2004; 22:307-28.
4. Bajorath J, Marken J S, Chalupny N J et al. Analysis of gp39/CD40 interactions to using molecular models and site-directed mutagenesis. Biochemistry 1995; 34(31): 9884-92.
5. Bajorath J. Detailed comparison of two molecular models of the human CD40 ligand with an x-ray structure and critical assessment of model-based mutagenesis and residue mapping studies. J Biol Chem 1998; 273(38):24603-9.
6. Bajorath J, Chalupny N J, Marken J S et al. Identification of residues on CD40 and its ligand which are critical for the receptor-ligand interaction. Biochemistry 1995; 34(6): 1833-44.
7. Singh J, Garber E, Van Vlijmen H et al. The role of polar interactions in the molecular recognition of CD40L with its receptor CD40. Protein Sci 1998; 7(5):1124-35.
8. Costello R T, Gastaut J A, Olive D. What is the real role of CD40 in cancer immunotherapy? Immunol Today 1999; 20(11):488-93.
9. Geldart T, Illidge T. Anti-CD 40 monoclonal antibody. Leuk Lymphoma 2005; 46(8):1105-1113.
10. Vonderheide R H. Prospect of targeting the CD40 pathway for cancer therapy. Clin Cancer Res 2007; 13(4): 1083-1088.
11. Werneburg B G, Zoog S J, Dang T T, Kehry M R, Crute J J. Molecular characterization of CD40 signaling intermediates. J Biol Chem 2001; 276(46):43334-43342.
12. Haswell L E, Glennie M J, Al-Shamkhani A. Analysis of the oligomeric requirement for signaling by CD40 using soluble multimeric forms of its ligand, CD154. Eur J Immunol 2001; 31(10):3094-3100.
13. Bishop G A, Hostager B S, Brown K D. Mechanisms of TNF receptor-associated factor (TRAF) regulation in B lymphocytes. J Leukoc Biol 2002; 72(1):19-23.
14. Pullen S S, Dang T T, Crute J J, Kehry M R. CD40 signaling through tumor necrosis factor receptor-associated factors (TRAFs). Binding site specificity and activation of downstream pathways by distinct TRAFs. J Biol Chem 1999; 274(20):14246-54.
15. Pullen S S, Labadia M E, Ingraham R H et al. High-affinity interactions of tumor necrosis factor receptor-associated factors (TRAFs) and CD40 require TRAF trimerization and CD40 multimerization. Biochemistry 1999; 38(31):10168-77.
16. van Mierlo G J, Den Boer A T, Medema J P et al. CD40 stimulation leads to effective therapy of CD40(−) tumors through induction of strong systemic cytotoxic T lymphocyte immunity. Proc Natl Acad Sci USA 2002; 99(8): 5561-5566.
17. Diehl L, Den Boer A T, Schoenberger S P et al. CD40 activation in vivo overcomes peptide-induced peripheral cytotoxic T-lymphocyte tolerance and augments antitumor vaccine efficacy. Nat Med 1999; 5(7):774-779.
18. French R R, Chan H T, Tutt A L, Glennie M J. CD40 antibody evokes a cytotoxic T cell response that eradicates lymphoma and bypasses T-cell help. Nat Med 1999; 5(5):548-53.
19. Sotomayor E M, Borrello I, Tubb E et al. Conversion of tumor-specific CD4+ T-cell tolerance to T-cell priming through in vivo ligation of CD40. Nat Med 1999; 5(7): 780-787.
20. Staveley-O'Carroll K, Schell T D, Jimenez M et al. In vivo ligation of CD40 enhances priming against the endogenous tumor antigen and promotes CD8+ T cell effector function in SV40 T antigen transgenic mice. J Immunol 2003; 171(2):697-707.
21. van Mierlo G J, Boonman Z F, Dumortier H M et al. Activation of dendritic cells that cross-present tumor-derived antigen licenses CD8+ CTL to cause tumor eradication. J Immunol 2004; 173(11):6753-6759.
22. Jackaman C, Lew A M, Zhan Y et al. Deliberately provoking local inflammation drives tumors to become their own protective vaccine site. Int Immunol 2008; 20(11):1467-1479.
23. Francisco J A, Donaldson K L, Chace D, Siegall C B, Wahl A F. Agonistic properties and in vivo antitumor activity of the anti-CD40 antibody SGN-14. Cancer Res 2000; 60(12):3225-31.
24. Hunter T B, Alsarraj M, Gladue R P, Bedian V, Antonia S J. An agonist antibody specific for CD40 induces dendritic cell maturation and promotes autologous anti-tumour T-cell responses in an in vitro mixed autologous tumour cell/lymph node cell model. Scand J Immunol 2007; 65(5):479-486.
25. Kelley S K, Gelzleichter T, Xie D et al. Preclinical pharmacokinetics, pharmacodynamics, and activity of a humanized anti-CD40 antibody (SGN-40) in rodents and non-human primates. Br J Pharmacol 2006; 148(8):1116-1123.
26. Law C L, Gordon K A, Collier J et al. Preclinical antilymphoma activity of a humanized anti-CD40 monoclonal antibody, SGN-40. Cancer Res 2005; 65(18):8331-8338.
27. Luqman M, Klabunde S, Lin K et al. The antileukemia activity of a human anti-CD40 antagonist antibody, HCD122, on human chronic lymphocytic leukemia cells. Blood 2008; 112(3):711-720.
28. Oflazoglu E, Stone I J, Brown L et al. Macrophages and Fc-receptor interactions contribute to the antitumour activities of the anti-CD40 antibody SGN-40. Br J Cancer 2009; 100(1):113-117.

29. Tai Y T, Podar K, Mitsiades N et al. CD40 induces human multiple myeloma cell migration via phosphatidylinositol 3-kinase/AKT/NF-kappa B signaling. Blood 2003; 101(7):2762-2769.
30. Tai Y T, Catley L P, Mitsiades C S et al. Mechanisms by which SGN-40, a humanized anti-CD40 antibody, induces cytotoxicity in human multiple myeloma cells: clinical implications. Cancer Res 2004; 64(8):2846-2852.
31. Tai Y T, Li X, Tong X et al. Human anti-CD40 antagonist antibody triggers significant antitumor activity against human multiple myeloma. Cancer Res 2005; 65(13): 5898-5906.
32. Khalil M, Vonderheide R H. Anti-CD40 agonist antibodies: Preclinical and clinical experience. Update on Cancer therapeutics 2007; 2(2):61-65.
33. Vonderheide R H, Dutcher J P, Anderson J E et al. Phase I study of recombinant human CD40 ligand in cancer patients. J Clin Oncol 2001; 19(13):3280-3287.
34. Vonderheide R H, Flaherty K T, Khalil M et al. Clinical activity and immune modulation in cancer patients treated with CP-870,893, a novel CD40 agonist monoclonal antibody. J Clin Oncol 2007; 25(7):876-883.
35. Bishop G A, Hostager B S, Brown K D. Mechanisms of TNF receptor-associated factor (TRAF) regulation in B lymphocytes. J Leukoc Biol 2002; 72(1):19-23.
36. Akagi T, Kaneko T, Kida T, Akashi M. Preparation and characterization of biodegradable nanoparticles based on poly(gamma-glutamic acid) with phenylalanine as a protein carrier. J Control Release 2005; 108(2-3):226-236.
37. Dominguez A L, Lustgarten J. Targeting the tumor microenvironment with antineu/anti-CD40 conjugated nanoparticles for the induction of antitumor immune responses. Vaccine 2010; 28(5):1383-1390.
38. Hatzifoti C, Bacon A, Marriott H, Laing P, Heath A W. Liposomal co-entrapment of CD40 mAb induces enhanced IgG responses against bacterial polysaccharide and protein. PLoS ONE 2008; 3(6):e2368.
39. Uto T, Wang X, Sato K et al. Targeting of Antigen to Dendritic Cells with Poly({gamma}-Glutamic Acid) Nanoparticles Induces Antigen-Specific Humoral and Cellular Immunity. The Journal of Immunology 2007; 178(5):2979-2986.
40. Ahonen C L, Wasiuk A, Fuse S et al. Enhanced efficacy and reduced toxicity of multifactorial adjuvants compared with unitary adjuvants as cancer vaccines. Blood 2008; 111(6):3116-3125.
41. Debbage P. Targeted drugs and nanomedicine: present and future. Curr Pharm Des 2009; 15(2):153-172.
42. Ellmark P, Andersson H, Abayneh S, Fenyo E M, Borrebaeck C A. Identification of a Strongly Activating Human Anti-CD40 Antibody That Suppresses HIV Type 1 Infection. AIDS Res Hum Retroviruses 2008.
43. Alexis, F., Pridgen, E., Molnar, L. K., & Farokhzad, O. C. Factors affecting the clearance and biodistribution of polymeric nanoparticles. *Mol Pharm* 5, 505-515 (2008).
44. Avgoustakis, K. Pegylated poly(lactide) and poly(lactide-co-glycolide) nanoparticles: preparation, properties and possible applications in drug delivery. *Curr Drug Deliv* 1, 321-333 (2004).
45. WO2010/024676. "Delivery of a CD40 agonist to a tumor draining lymph node of a subject"
46. Dobrovolskaia, M. A., Aggarwal, P., Hall, J. B., & McNeil, S. E. Preclinical studies to understand nanoparticle interaction with the immune system and its potential effects on nanoparticle biodistribution. *Mol Pharm* 5, 487-495 (2008).
47. Uto, T. et al., Targeting of Antigen to Dendritic Cells with Poly({gamma}-Glutamic Acid) Nanoparticles Induces Antigen-Specific Humoral and Cellular Immunity. *The Journal of immunology* 178, 2979-2986 (2007).
48. Bugelski, P. J., Achuthanandam, R., Capocasale, R. J., Treacy, G., & Bouman-Thio, E. Monoclonal antibody-induced cytokine-release syndrome. *Expert Rev Clin Immunol* 5, 499-521 (2009).
49. Fransen, M. F., Sluijter, M., Morreau, H., Arens, R., & Melief, C. J. Local reprogramming of CD8 T cells and systemic tumor eradication without toxicity via slow release and local delivery of agonistic CD40 antibody. *Clin Cancer Res* (2011).

The invention claimed is:

1. A pharmaceutical composition comprising:
   (a) an anti-CD40 antibody or antigen-binding fragment thereof which is a CD40 agonist; and
   (b) nanoparticles;
   in a pharmaceutically acceptable diluent, carrier or excipient,
   wherein the nanoparticles comprise gamma polyglutamic acid (γPGA), and wherein the antibody or antigen-binding fragment thereof and the nanoparticles are provided in a mixture.

2. A composition according to claim 1 further comprising an antigen.

3. A composition according to claim 2 wherein the antigen is a cancer cell antigen.

4. A method for stimulating the immune system in a subject comprising administering to the subject a composition according to claim 1.

5. The method of claim 4, wherein the subject has cancer.

6. The method of claim 4, wherein the subject has a viral infection.

7. The method of claim 4, wherein the subject has an autoimmune disease.

8. A kit of parts comprising:
   (a) an anti-CD40 antibody or antigen-binding fragment thereof which is a CD40 agonist; and
   (b) nanoparticles
   wherein the nanoparticles comprise polyglutamic acid (γPGA), and wherein the antibody or antigen-binding fragment thereof and the nanoparticles are provided in a mixture.

9. A kit of parts according to claim 8 wherein components (a) and (b) are separately formulated in a pharmaceutically-acceptable excipient, diluent or carrier.

10. A method for producing a pharmaceutical composition according to claim 1 comprising admixing the antibody or antigen binding fragment thereof and nanoparticles together with a pharmaceutically acceptable diluent, carrier or excipient.

* * * * *